US012766206B2

(12) United States Patent
Temple

(10) Patent No.: US 12,766,206 B2
(45) Date of Patent: Oct. 20, 2026

(54) AUTOMATED ULTRAVIOLET LIGHT HAND STERILIZATION STATION

(71) Applicant: Garrett Temple, Santa Cruz, CA (US)

(72) Inventor: Garrett Temple, Santa Cruz, CA (US)

( * ) Notice: Subject to any disclaimer, the term of this patent is extended or adjusted under 35 U.S.C. 154(b) by 345 days.

(21) Appl. No.: 18/598,686

(22) Filed: Mar. 7, 2024

(65) Prior Publication Data

US 2024/0342324 A1 Oct. 17, 2024

Related U.S. Application Data

(60) Provisional application No. 63/455,835, filed on Mar. 30, 2023.

(51) Int. Cl.

| | |
|---|---|
| ***A61L 2/10*** | (2026.01) |
| ***A61L 2/24*** | (2006.01) |
| ***A61L 2/26*** | (2006.01) |
| *A61L 103/05* | (2026.01) |

(52) U.S. Cl.

CPC .................. *A61L 2/10* (2013.01); *A61L 2/24* (2013.01); *A61L 2/26* (2013.01); *A61L 2103/05* (2026.01); *A61L 2202/11* (2013.01); *A61L 2202/14* (2013.01)

(58) Field of Classification Search

CPC ..... A61L 2/10; A61L 2/24; A61L 2/26; A61L 2103/05; A61L 2202/11; A61L 2202/14

See application file for complete search history.

(56) References Cited

U.S. PATENT DOCUMENTS

| | | | | |
|---|---|---|---|---|
| 2021/0369881 | A1* | 12/2021 | Hayden | A61L 2/10 |
| 2022/0062454 | A1* | 3/2022 | Flaherty | A61L 2/084 |

* cited by examiner

*Primary Examiner* — Nicole M Ippolito

(74) *Attorney, Agent, or Firm* — Cohen IP Law Group P.C.; Michael N. Cohen

(57) ABSTRACT

An automated ultraviolet (UV) light hand sanitizing system. The automated hand sanitization system includes a housing for attachment to the wall or other suitable structure, a UV sterilization system on an angled underside of the housing, a motion sensing system to detect the user's hands and to begin the UV sterilization process, a timer system to track the time during the UV sterilization process, and a photovoltaic energy system to power the system.

20 Claims, 3 Drawing Sheets

AUTOMATED ULTRAVIOLET LIGHT HAND STERILIZATION STATION

FIELD OF THE INVENTION

This invention relates to cleaning systems, including an automated ultraviolet light hand sterilization station.

BACKGROUND

It is well known that diseases, including viral and/or bacterial infections, may be transmitted through touch. As such, the medical community recommends washing one's hands throughout the day, especially if contact has been made with an infected person.

However, hand washing using only soap does not always properly remove this threat.

Accordingly, there is a need for an automated ultraviolet light hand sterilization system.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF EXEMPLARY EMBODIMENTS

In general, the system according to exemplary embodiments hereof includes an automated ultraviolet (UV) light hand sterilization system.

Figure 1:
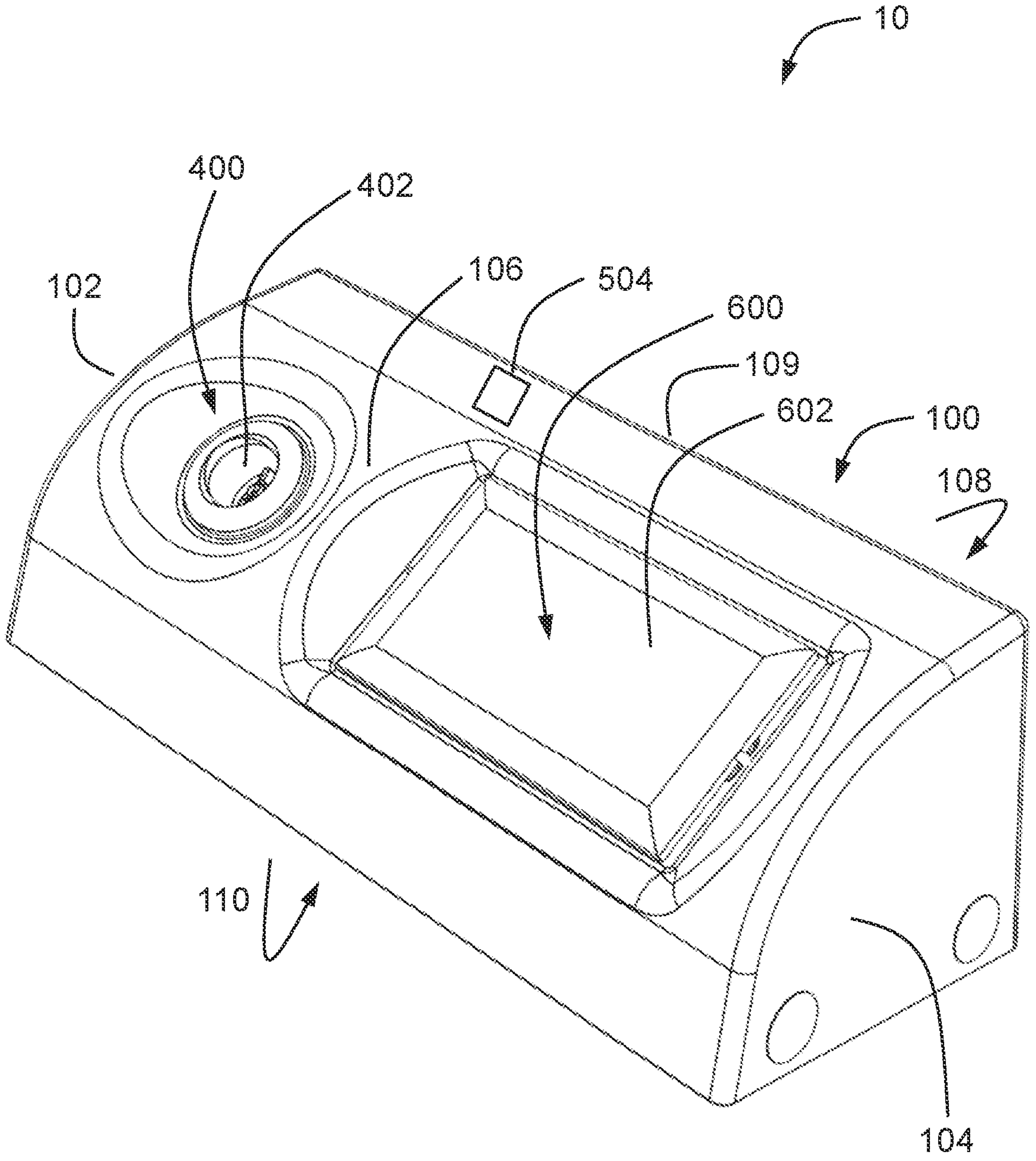
FIG. 1 shows a schematic of a hand sterilization system according to exemplary embodiments hereof.
Figure 2:
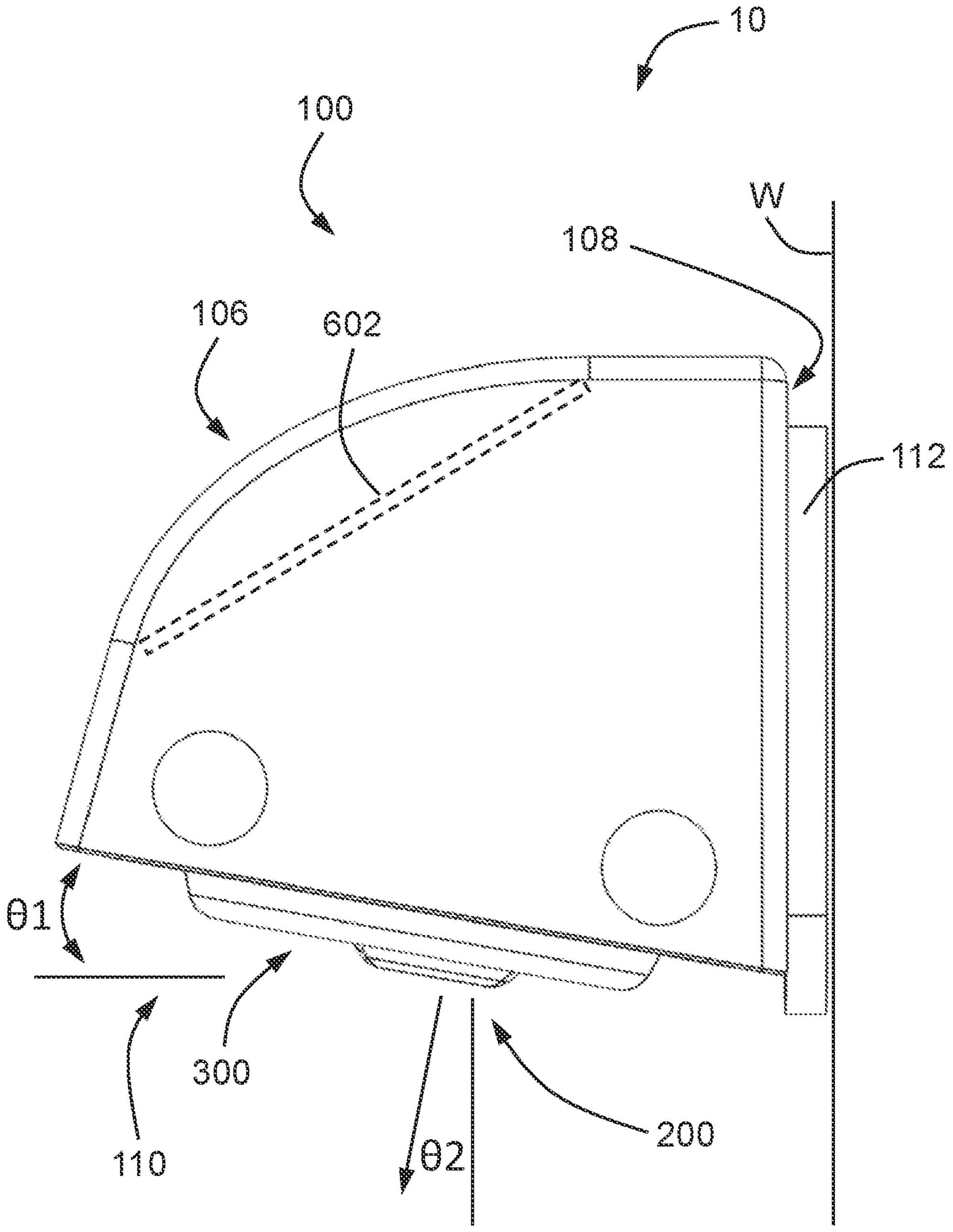
FIG. 2 shows a side view of a hand sterilization system according to exemplary embodiments hereof.
Figure 3:
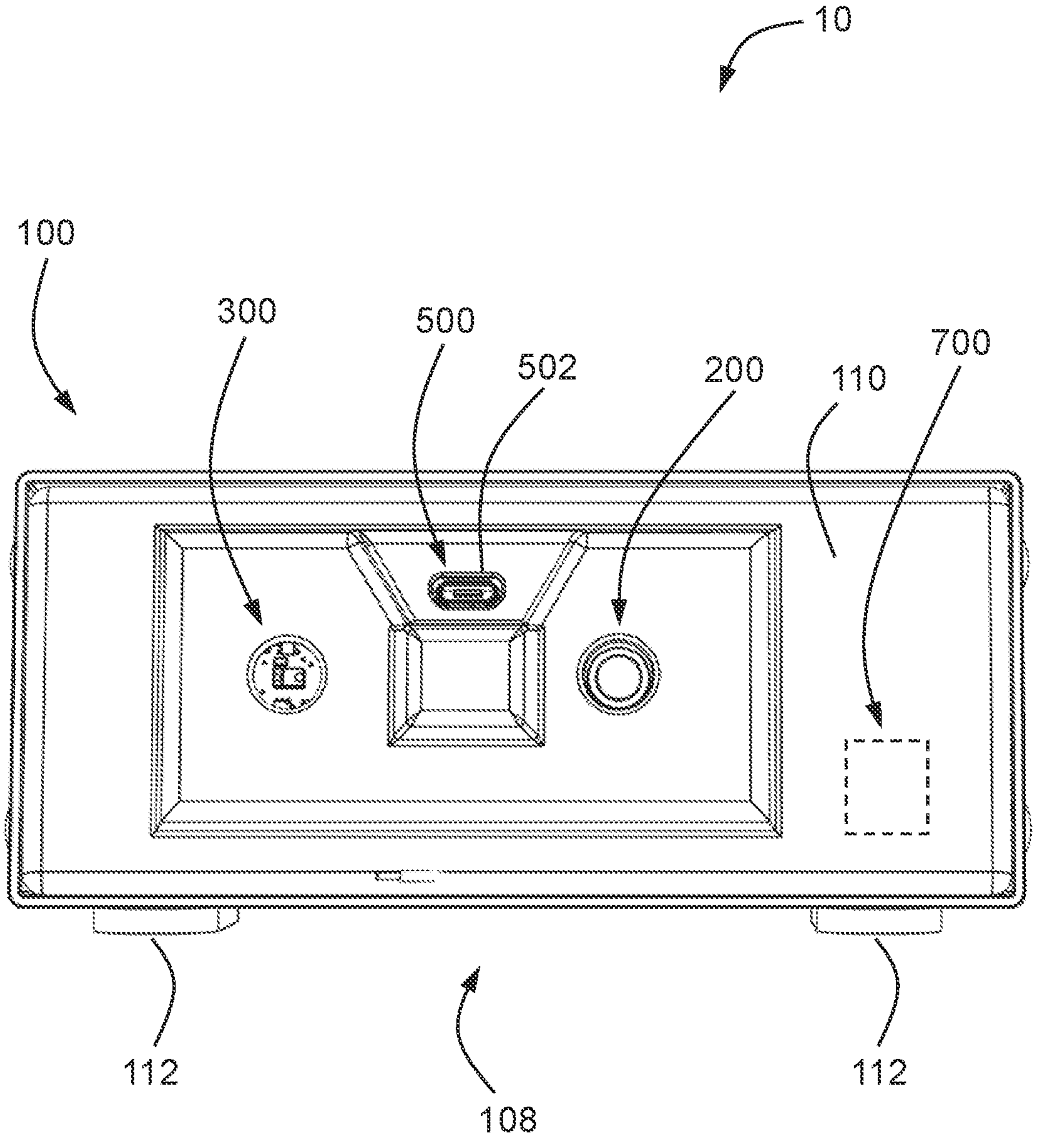
FIG. 3 shows an underside view of a hand sterilization system according to exemplary embodiments hereof.

In one exemplary embodiment hereof, as shown in FIGS. 1, 2, and 3, the automated ultraviolet (UV) light hand sanitizing system 10 (also referred to as simply the system 10) includes a housing 100, an ultraviolet light (UV) sterilization system 200, a motion sensing system 300, a timer system 400, a power supply 500, a photovoltaic energy system 600, and a controller 700. The system 10 also may include other elements as necessary for the system 10 to perform its functionalities.

In general, the housing 100 is attached to a wall or other support structure, preferably above and/or in close proximity to a sink or other type of hand cleaning station. The motion sensing system 300 is designed to sense the presence of a user's hands within the operating perimeter of the UV sterilization system 200, and upon such sensing, the UV sterilization system 200 is triggered to emit UV sanitizing light (e.g., onto the user's hands). The timer system 400 is simultaneously triggered to begin a countdown (e.g., a twenty second countdown) for the user to continue holding his/her hands within the UV sterilization light, and upon hitting zero, the timer system 400 indicates that the sterilization process has been completed. The power supply 500 includes any type of power supply (e.g., preferably rechargeable) and may include a photovoltaic energy system 600 to generate additional power for the system 10 to use during operation. The controller 700 is configured with the various elements of the system 10 to generally control its functionalities.

In some embodiments, as shown in FIG. 1, the system 10 includes a housing 100 including a left side 102, a right side 104, a front side 106, a back side 108, a top 109, and a bottom or underside 110. In some embodiments, the housing 100 is generally rectangular with a generally convex front side 106 that transitions from a generally vertical or near vertical portion (e.g., preferably 80°-90° upright at or near the bottom 110) to a generally horizontal or near horizontal top 109 of the housing 100 with the convex transitional portion 106 therebetween. This convex shaped front side 106 enables users of different heights to view the system 10 and the system's elements (e.g., readouts, control mechanisms, etc.) on the convex surface 106 by positioning the front side elements in a generally upward facing orientation. This convex portion 106 also may provide a base for the photovoltaic energy system 600 including one or more photovoltaic cells 602 that may be properly oriented when integrated into the convex portion 106 (e.g., at or near 45° with respect to the horizontal) such that the system 10 and the photovoltaic cells 602 may be oriented for maximum light exposure. This is shown in FIG. 2.

In some embodiments, as shown in FIG. 1, the back side 108 may be secured to a wall W or other type of support structure for the system 10 use. In some embodiments, the back side 108 includes one or more mounting feet 112 configured to rest against the wall W and be secured thereto. The mounting feet 112 may be secured to the wall W using double-sided tape, mounting screws, bolts, adhesive, latches, other types of attachment mechanisms, and any combinations thereof.

In some embodiments, as shown in FIGS. 2 and 3, the motion sensing system 300 is positioned on the underside 110 to sense motion from this perspective. In this way, when a user places his/her hands under the underside 110 of the housing 100, the motion sensing system 300 may sense the motion and presence of the hands. In some instances, the system 10 is positioned above a sink or other hand cleaning station such that after (or before) the user washes his/her hands using the sink, the user also may utilize the system 10 to sterilize his/her hands. In other instances, the system 10 may be placed in other locations that may be beneficial to a user for sterilizing his/her hands. The motion sensing system 300 may include an infrared proximity sensor or other adequate type(s) of motion sensing devices.

In some embodiments, as shown in FIG. 2, the housing's underside 110 may extend upward at an angle θ1 from the horizontal as it extends away from the wall W. This may enable users of different height to easily position his/her hands underneath the system 10 to trigger the motion sensing system 300. In addition, this may angle the UV light sterilization system 200 (described below) to be oriented at an angle θ2 with respect to the vertical. As such, the light emitted by the sterilization system 200 also may be angled outward from the vertical enabling users of different heights to adequately position their hands beneath the sterilization system 200 to be adequately radiated.

In some embodiments, the angle θ1 is about 0° to about 45°, and preferably about 5° to about 35°, and more preferably about 10° to about 30° and more preferably about 15° to about 20°. In some embodiments, the angle θ2 is about 0° to about 45°, and preferably about 5° to about 35°, and more preferably about 10° to about 30° and more preferably about 15° to about 20°.

In some embodiments, upon sensing motion, the motion sensing system 300 causes the UV light sterilization system 200 to activate and to emit UV light downward and onto the user's hands. This may be controlled by the controller 700. The UV light emitted by the system 200 may radiate the microorganism's genetic material (DNA and RNA) on the user's hands, thereby destroying the cell's ability to reproduce. In this way, the user's hands may be sterilized.

In some embodiments, the user may be instructed, either via a display on the housing or via an audio message, to move his/her hands periodically (e.g., in a rubbing motion) within the UV light such that each surface of the user's hands may be sterilized by the light. In some embodiments, the user also may be instructed that the process will last a specific amount of time (e.g., twenty seconds) and that he/she must hold his/her hands within the UV light for the entire amount of time to be fully sterilized.

In some embodiments, as shown in FIG. 1, the timer system 400 includes an indicator 402, such as, without limitation, an LED light that may indicate when the countdown has begun and when the countdown has completed. For example, the indicator 402 may turn green when the countdown has begun and may turn red when the countdown has completed. Other types of indications also are contemplated (e.g., audio beeps, buzzers, vibrating devices, etc.). In some embodiments, the indicator 402 may include a display (e.g., an alphanumerical display, a touchscreen, a readout, etc.) that may show the numerical countdown, e.g., if the countdown time is 20 seconds, the indicator 402 may show the number 20 followed one second later by the number 19 followed one second later by the number 18 and so on until the countdown reaches zero.

In some embodiments, the indicator 402 (e.g., a touchscreen) also may provide instructions, such as, textual instructions, animated instructions, video instructions, audio instruction, other types of instructions, and/or any combinations thereof.

In some embodiments, if the user removes his/her hands from within the UV light prior to the completion of the countdown, the motion sensing system 300 may recognize this and cause the indicator 402 to change its indication from green to red, to beep, to display a message on the display stating that the sterilization process has not been adequately completed, etc. In addition, the timer system 400 may pause the countdown if the user removes his/her hands from the UV light and may resume the countdown once the user's hands have been detected again in the correct area for sterilization. In this case, it is preferable that the UV light sterilization system 200 continue to emit sterilizing UV light during any pause in the countdown so that the user may continue immediately with the sterilization process once returning his/her hands to the illumination area. In other embodiments, however, the UV light sterilization system 200 may temporarily cease emitting UV light if and when the user removes his/her hands from the proper position, and may resume emitting UV light upon the user repositioning his/her hands in the proper position for complete sterilization.

In some embodiments, as shown in FIG. 3, the system 10 includes a power supply 500 includes a rechargeable power source such as a battery. In other embodiments, the power supply 500 may include a voltage transformer that may be plugged into a wall outlet or other type of power supply to provide the proper voltage and/or current to the system 10. In some embodiments, the power supply 500 includes a charging port 502 that may be connected to an outside power supply (e.g., a wall outlet) such that the internal power supply 500 may be charged. In some embodiments, the power supply 500 may be removed from the housing 100 to be recharged and/or replaced.

In some embodiments, as shown in FIG. 1, the power supply 500 also may include a photovoltaic energy system 600 including one or more photovoltaic cells 602 that generate energy when irradiated by light.

In some embodiments, the system 10 includes a light detector 504, e.g., positioned on its front side 106, configured to sense when the system 10 is within a lighted area and to turn the system 10 on in such a case (e.g., when a user enters a bathroom and turns on the lights). In other embodiments, the system 10 may include an On/Off switch to turn the system 10 on and/or off.

In some embodiments, the controller 700 includes a microprocessor, a microcontroller, a CPU, a computer, any other type(s) of controllers, and any combinations thereof.

In some embodiments, the system 10 includes a soap dispenser, e.g., configured on the underside 110 of the housing 100.

In some embodiments, the system 10 includes anti-theft mechanisms, e.g., sensors configured with the mounting feet 112 that may detect when the mounting feet 112 have been detached from the wall W.

In some embodiments, the system 10 includes features designed for the visually impaired, such as, without limitation, a sound chip and speaker integration.

It is understood that any aspect and/or element of any embodiment of the system 10 described herein or otherwise may be combined with any other aspect and/or element of any other embodiment described herein or otherwise in any way to form additional embodiments of the system 10 all of which are within the scope of the system 10.

Where a process is described herein, those of ordinary skill in the art will appreciate that the process may operate without any user intervention. In another embodiment, the process includes some human intervention (e.g., a step is performed by or with the assistance of a human).

As used herein, including in the claims, the phrase "at least some" means "one or more," and includes the case of only one. Thus, e.g., the phrase "at least some ABCs" means "one or more ABCs" and includes the case of only one ABC.

As used herein, including in the claims, term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

As used in this description, the term "portion" means some or all. So, for example, "A portion of X" may include some of "X" or all of "X". In the context of a conversation, the term "portion" means some or all of the conversation.

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

In general, as used herein, including in the claims, unless the word “only” is specifically used in a phrase, it should not be read into that phrase.

As used herein, including in the claims, the phrase “distinct” means “at least partially distinct.” Unless specifically stated, distinct does not mean fully distinct. Thus, e.g., the phrase, “X is distinct from Y” means that “X is at least partially distinct from Y,” and does not mean that “X is fully distinct from Y.” Thus, as used herein, including in the claims, the phrase “X is distinct from Y” means that X differs from Y in at least some way.

It should be appreciated that the words “first,” “second,” and so on, in the description and claims, are used to distinguish or identify, and not to show a serial or numerical limitation. Similarly, letter labels (e.g., “(A)”, “(B)”, “(C)”, and so on, or “(a)”, “(b)”, and so on) and/or numbers (e.g., “(i)”, “(ii)”, and so on) are used to assist in readability and to help distinguish and/or identify and are not intended to be otherwise limiting or to impose or imply any serial or numerical limitations or orderings. Similarly, words such as “particular,” “specific,” “certain,” and “given,” in the description and claims, if used, are to distinguish or identify, and are not intended to be otherwise limiting.

As used herein, including in the claims, the terms “multiple” and “plurality” mean “two or more,” and include the case of “two.” Thus, e.g., the phrase “multiple ABCs,” means “two or more ABCs,” and includes “two ABCs.” Similarly, e.g., the phrase “multiple PQRs,” means “two or more PQRs,” and includes “two PQRs.”

The present invention also covers the exact terms, features, values and ranges, etc. in case these terms, features, values and ranges etc. are used in conjunction with terms such as about, around, generally, substantially, essentially, at least etc. (i.e., “about 3” or “approximately 3” shall also cover exactly 3 or “substantially constant” shall also cover exactly constant).

As used herein, including in the claims, singular forms of terms are to be construed as also including the plural form and vice versa, unless the context indicates otherwise. Thus, it should be noted that as used herein, the singular forms “a,” “an,” and “the” include plural references unless the context clearly dictates otherwise.

Throughout the description and claims, the terms “comprise”, “including”, “having”, and “contain” and their variations should be understood as meaning “including but not limited to” and are not intended to exclude other components unless specifically so stated.

It will be appreciated that variations to the embodiments of the invention can be made while still falling within the scope of the invention. Alternative features serving the same, equivalent, or similar purpose can replace features disclosed in the specification, unless stated otherwise. Thus, unless stated otherwise, each feature disclosed represents one example of a generic series of equivalent or similar features.

The present invention also covers the exact terms, features, values, and ranges, etc. in case these terms, features, values, and ranges etc. are used in conjunction with terms such as about, around, generally, substantially, essentially, at least etc. (i.e., “about 3” shall also cover exactly 3 or “substantially constant” shall also cover exactly constant).

Use of exemplary language, such as “for instance”, “such as”, “for example” (“e.g.,”) and the like, is merely intended to better illustrate the invention and does not indicate a limitation on the scope of the invention unless specifically so claimed.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

What is claimed is:

1. A hand sterilizing system comprising:
- a housing including a front side and an underneath side, the underneath side comprising an exterior, downward-facing surface of the housing;
- a motion sensor adapted to sense motion within an open area beneath the underneath side;
- a light emitting system configured with the underneath side and adapted to emit sterilizing light downward from the underneath side into the open area, wherein the open area is bounded above by the underneath side and is otherwise unbounded by any portion of the hand sterilizing system;
- wherein when the motion sensor detects motion within the open area, the light emitting system is triggered to emit the sterilizing light downward into the open area.

2. The hand sterilizing system of claim 1 wherein the motion sensor is adapted to sense a first motion that triggers the light emitting system to emit first sterilizing light, and to sense a stoppage of the first motion upon which the light emitting system is triggered to cease emitting the first sterilizing light.

3. The hand sterilizing system of claim 1 further comprising a timer that tracks a time period of the sterilizing light emission.

4. The hand sterilizing system of claim 3 wherein the timer includes a timing countdown device.

5. The hand sterilizing system of claim 4 wherein the light emitting system is triggered to cease emitting sterilizing light when the timing countdown device reaches zero.

6. The hand sterilizing system of claim 4 wherein the motion sensor is adapted to sense a first motion that triggers the light emitting system to emit first sterilizing light, and to sense a stoppage of the first motion upon which the light emitting system is triggered to cease emitting the first sterilizing light and the timing countdown device is caused to stop counting.

7. The hand sterilizing system of claim 1 wherein the front side follows a convex contour from a bottom of the first front side to a top of the front side.

8. The hand sterilizing system of claim 1 further comprising at least one photovoltaic cell adapted to provide power to the hand sterilizing system.

9. The hand sterilizing system of claim 1 wherein the underneath side is at an angle of about 15° to 20° with respect to a horizontal.

10. The hand sterilizing system of claim 1 wherein the sterilizing light includes ultraviolet light.

11. A hand sterilizing system comprising:
- a housing including a front side and an underneath side;
- a motion sensor adapted to sense motion beneath the underneath side;
- a light emitting system configured with the underneath side; and
- at least one photovoltaic cell adapted to provide power to the hand sterilizing system;
- wherein when the motion sensor detects motion, the light emitting system is triggered to emit sterilizing light; and wherein the front side follows a convex contour from a bottom of the first front side to a top of the front side and wherein the at least one photovoltaic cell is configured with a surface of the convex contour.

12. The hand sterilizing system of claim 11 wherein the configuration of the at least one photovoltaic cell with the surface of the convex contour positions the at least one photovoltaic cell at an angle of about 45° with respect to a horizontal.

13. A hand sterilizing system comprising:

a housing including a front side and an underneath side, the underneath side comprising an exterior, downward-facing surface of the housing;

a motion sensor adapted to sense motion beneath the underneath side;

a light emitting system configured with the underneath side and adapted to emit ultraviolet (UV) sterilizing light downward from the underneath side, wherein an entirety of the UV sterilizing light emitted by the hand sterilizing system is emitted downward from the underneath side;

wherein when the motion sensor detects motion beneath the underneath side, the light emitting system is triggered to emit the UV sterilizing light.

14. The hand sterilizing system of claim 13 wherein the motion sensor is adapted to sense the motion within an open area beneath the underneath side, and wherein the open area is bounded above by the underneath side and is otherwise unbounded by any portion of the hand sterilizing system.

15. The hand sterilizing system of claim 13 further comprising a timer including a timing countdown device, wherein the timing countdown device is caused to pause counting when the motion sensor senses a stoppage of motion beneath the underneath side, and to resume counting when the motion sensor senses motion beneath the underneath side.

16. The hand sterilizing system of claim 15 wherein the light emitting system continues to emit the UV sterilizing light while the timing countdown device is paused.

17. The hand sterilizing system of claim 13 wherein the housing further includes a back side adapted to be secured to a support structure.

18. The hand sterilizing system of claim 17 wherein the underneath side extends upward at an angle from a horizontal as the underneath side extends away from the back side.

19. The hand sterilizing system of claim 13 further comprising a light detector configured to sense when the hand sterilizing system is within a lighted area and to turn the hand sterilizing system on.

20. The hand sterilizing system of claim 13 wherein the front side follows a convex contour from a bottom of the front side to a top of the front side, the hand sterilizing system further comprising at least one photovoltaic cell configured with a surface of the convex contour and adapted to provide power to the hand sterilizing system.

* * * * *